US011439432B2

(12) United States Patent
Sweeney et al.

(10) Patent No.: US 11,439,432 B2
(45) Date of Patent: Sep. 13, 2022

(54) HANDLE ATTACHMENT FOR FLUID DELIVERY NEEDLE AND METHOD OF USE THEREOF

(71) Applicant: Spinal Generations, LLC, Mokena, IL (US)

(72) Inventors: Patrick J. Sweeney, Flossmoor, IL (US); Matthew V. Leyden, St. Paul, MN (US); Ray Hines, Mokena, IL (US)

(73) Assignee: Spinal Generations, LLC, Mokena, IL (US)

(*) Notice: Subject to any disclaimer, the term of this patent is extended or adjusted under 35 U.S.C. 154(b) by 231 days.

(21) Appl. No.: 16/844,125

(22) Filed: Apr. 9, 2020

(65) Prior Publication Data
US 2021/0315611 A1    Oct. 14, 2021

(51) Int. Cl.
| A61B 17/34 | (2006.01) |
| A61B 5/15 | (2006.01) |
| A61B 17/00 | (2006.01) |

(52) U.S. Cl.
CPC .... *A61B 17/3472* (2013.01); *A61B 5/150732* (2013.01); *A61B 2017/00473* (2013.01)

(58) Field of Classification Search
CPC .... A61B 5/150732; A61B 2017/00424; A61B 2017/0046; A61B 2017/00469; A61B 2017/00473; A61B 17/06061; A61B 17/062; A61B 17/3472; B25G 1/005; B25G 1/06; B25G 1/063; B25G 1/105
See application file for complete search history.

(56) References Cited

U.S. PATENT DOCUMENTS

| 5,372,583 | A | * | 12/1994 | Roberts | A61M 25/06 |
| | | | | | 600/567 |
| 7,634,307 | B2 | | 12/2009 | Sweeney | |
| 7,713,273 | B2 | * | 5/2010 | Krueger | A61B 17/8811 |
| | | | | | 606/94 |
| 7,953,472 | B2 | | 5/2011 | Sweeney | |
| 8,870,836 | B2 | | 10/2014 | Sweeney | |
| 9,044,284 | B2 | | 6/2015 | Sweeney | |
| 9,433,400 | B2 | * | 9/2016 | Miller | A61B 17/3476 |
| 9,445,852 | B2 | | 9/2016 | Sweeney | |
| 9,603,644 | B2 | | 3/2017 | Sweeney | |
| 9,615,863 | B2 | | 4/2017 | Sweeney | |
| 9,808,355 | B2 | | 11/2017 | Sweeney | |
| 9,949,777 | B2 | | 4/2018 | Sweeney | |
| 10,188,440 | B2 | | 1/2019 | Sweeney | |
| D855,804 | S | | 8/2019 | Sweeney et al. | |
| 10,517,660 | B2 | | 12/2019 | Sweeney | |
| D882,085 | S | | 4/2020 | Sweeney et al. | |

(Continued)

*Primary Examiner* — Larry E Waggle, Jr.
(74) *Attorney, Agent, or Firm* — Foley & Lardner LLP

(57) ABSTRACT

A system including includes an intraosseous needle and a handle. The intraosseous needle includes a distal end configured for insertion into a bone and a proximal end configured to extend from the bone. The handle is configured to releasably engage the intraosseous needle. The handle includes a cylindrical body portion, a handle portion, and a channel. The cylindrical body portion includes a distal end configured to receive the proximal end of the intraosseous needle. The handle portion extends from the cylindrical body portion and has a bulb-like cross-sectional shape and opposing first and second substantially planar surfaces. The channel is configured to receive the proximal end of the intraosseous needle.

21 Claims, 13 Drawing Sheets

(56) References Cited

U.S. PATENT DOCUMENTS

| | | |
|---|---|---|
| 10,653,470 B2 | 5/2020 | Sweeney |
| 2011/0224476 A1 | 9/2011 | Sweeney |
| 2014/0142584 A1 | 5/2014 | Sweeney |
| 2018/0206898 A1 | 7/2018 | Sweeney |
| 2019/0184097 A1 | 6/2019 | Sweeney et al. |

* cited by examiner

HANDLE ATTACHMENT FOR FLUID DELIVERY NEEDLE AND METHOD OF USE THEREOF

BACKGROUND

The present disclosure relates generally to the field of devices and methods for delivering substances to bone. More particularly, the present disclosure concerns devices and methods for performing an intraosseous infusion.

An intraosseous infusion is a procedure in which fluid, such as a medication or anesthetic, is delivered to the interior of a bone. When intravenous infusions are difficult or impossible due to tissue damage or small venous size, intraosseous infusions may be preferred because the interior of a bone provides a relatively large and reliable entry point into the venous system that is protected by a rigid bone cortex. Intraosseous infusions are therefore often used for battlefield or civilian trauma patients and in children who require prompt delivery of fluids such as medications or anesthetics.

An intraosseous infusion is performed by inserting an intraosseous needle into a patient's bone, more particularly through the bone's rigid cortex to a spongy interior section where fluid can be delivered. Once the intraosseous needle is inserted into the patient's bone, fluid is delivered to the interior of the bone through the needle. Conventionally, an intraosseous needle has an open tip through which the fluid is delivered.

SUMMARY

One embodiment relates to a system. The system includes an intraosseous needle and a handle. The intraosseous needle includes a distal end configured for insertion into a bone and a proximal end configured to extend from the bone. The handle is configured to releasably engage the intraosseous needle. The handle includes a cylindrical body portion, a handle portion, and a channel. The cylindrical body portion includes a distal end configured to receive the proximal end of the intraosseous needle. The handle portion extends from the cylindrical body portion and has a bulb-like cross-sectional shape and opposing first and second substantially planar surfaces. The channel is configured to receive the proximal end of the intraosseous needle.

Another embodiment relates to a handle configured to engage an intraosseous needle including a distal end configured for insertion into a bone and a proximal end configured to extend from the bone. The handle includes a cylindrical body portion, a flared handle portion, and a channel. The cylindrical body portion includes a distal end configured to receive the proximal end of the intraosseous needle. The cylindrical body portion defines a longitudinal axis of the handle. The flared handle portion has a width larger than a width of the cylindrical body portion. The flared handle portion includes a first lobe, a second lobe, and a notch positioned between the first lobe and the second lobe. A channel extends between a proximal end of the flared handle portion and the distal end of the cylindrical body portion along the longitudinal axis.

Another embodiment relates to a method for inserting a medical device into the interior of a bone. The method includes coupling a driving shaft to an intraosseous needle. The method includes engaging the driving shaft and a proximal end of the intraosseous needle with a channel of a handle. The handle includes a cylindrical body portion and a flared handle portion. The cylindrical body portion includes a distal end configured to receive the proximal end of the intraosseous needle. The flared handle portion has a width larger than a width of the cylindrical body portion. The flared handle portion includes a first lobe, a second lobe, and a notch positioned between the first lobe and the second lobe. The method includes actuating the handle to insert the intraosseous needle into the bone. The method includes pushing on a portion of the distal end of the driving shaft that protrudes into the notch to disengage the driving shaft from the handle. Removing the handle from the driving shaft allows the driving shaft to be coupled to a power driver and/or allows the handle to be used to provide countertorque or as a forceps.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1:
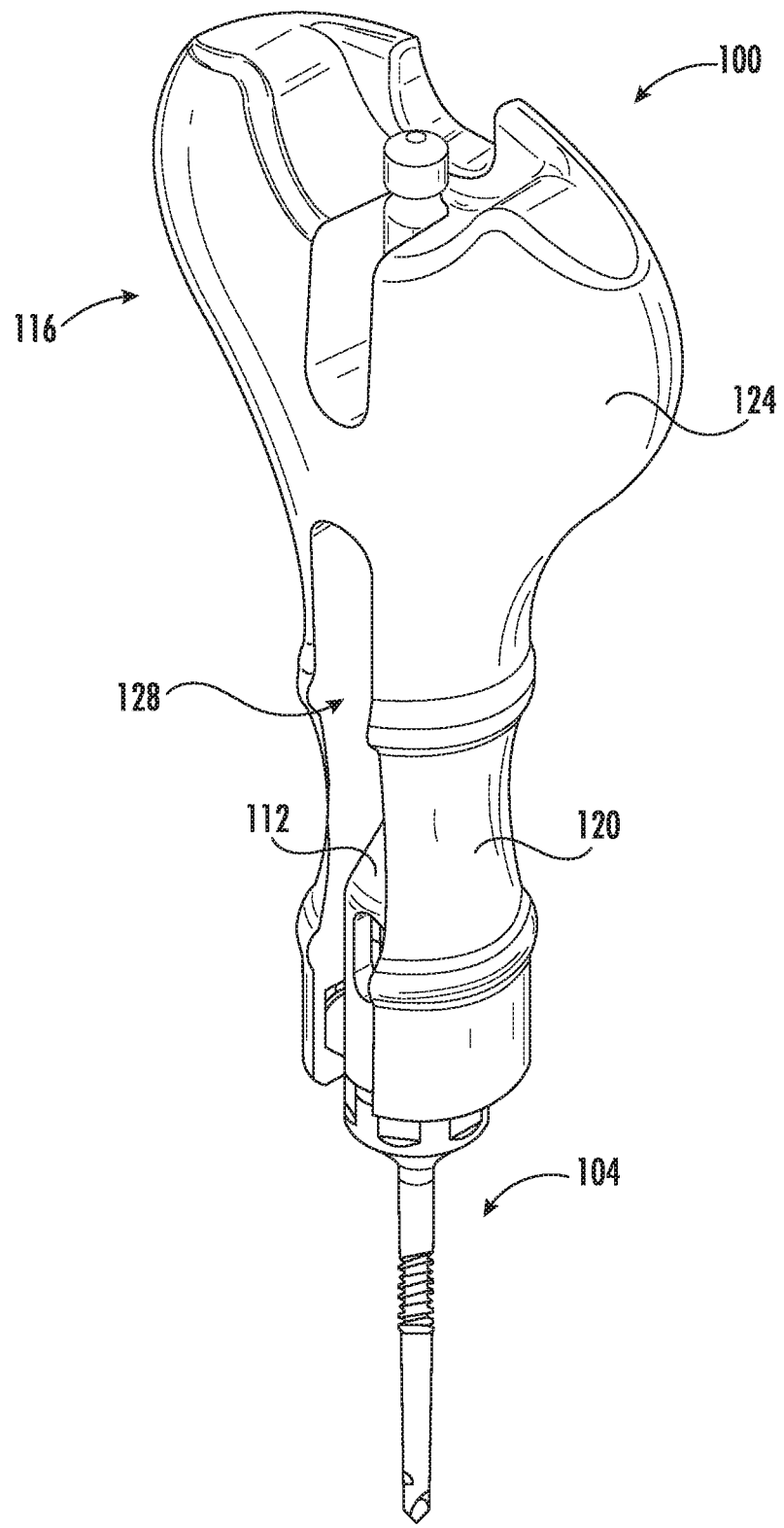
FIG. 1 is a perspective view of an intraosseous needle assembly having a needle, a stylet, a driving shaft, and a handle, in an operating configuration, according to an exemplary embodiment.

FIG. 1 shows a perspective view of an intraosseous needle assembly 100 in a first operating configuration according to an exemplary embodiment. The intraosseous needle assembly 100 includes a needle 104, a stylet 108 (FIG. 2), a driving shaft 112, and a handle 116. The handle 116 includes a cylindrical body portion 120, a handle portion 124, and a channel 128.

Figure 2:
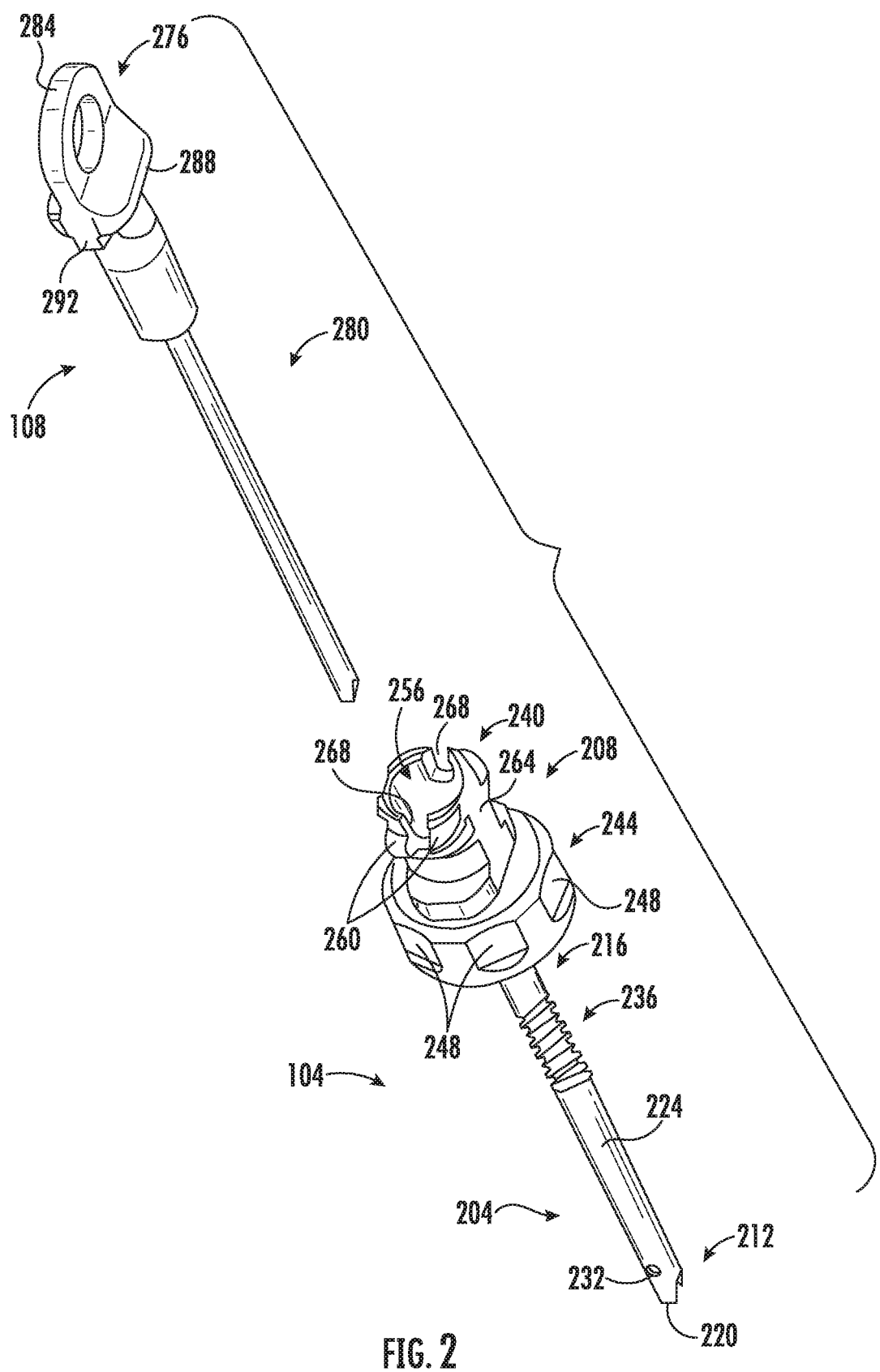
FIG. 2 is an exploded view of the needle and the stylet of the intraosseous needle assembly of FIG. 1, according to an exemplary embodiment.
Figure 9:
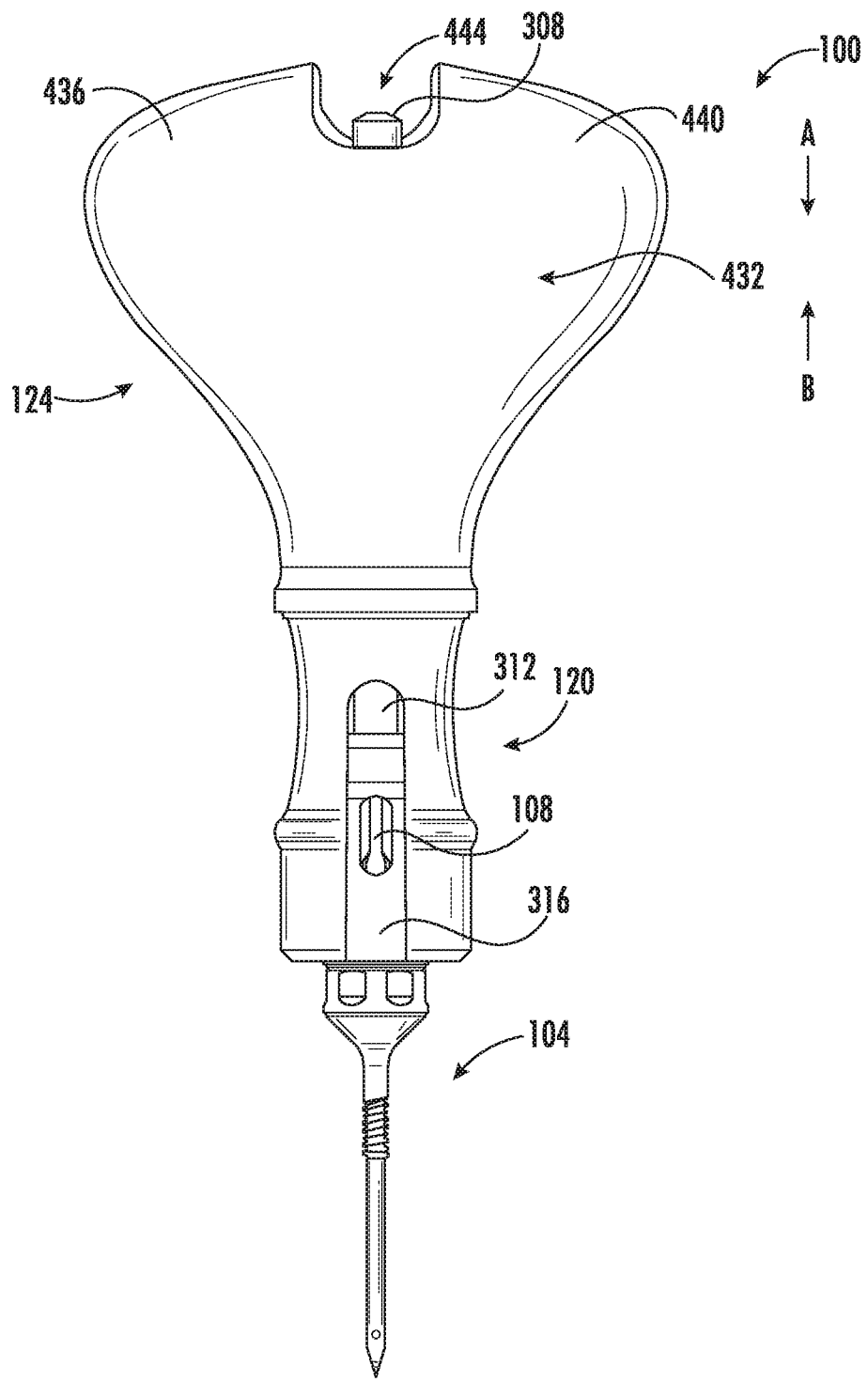
FIG. 9 is a rear view of the intraosseous needle assembly in the operating configuration of FIG. 1, according to an exemplary embodiment.
Figure 10:
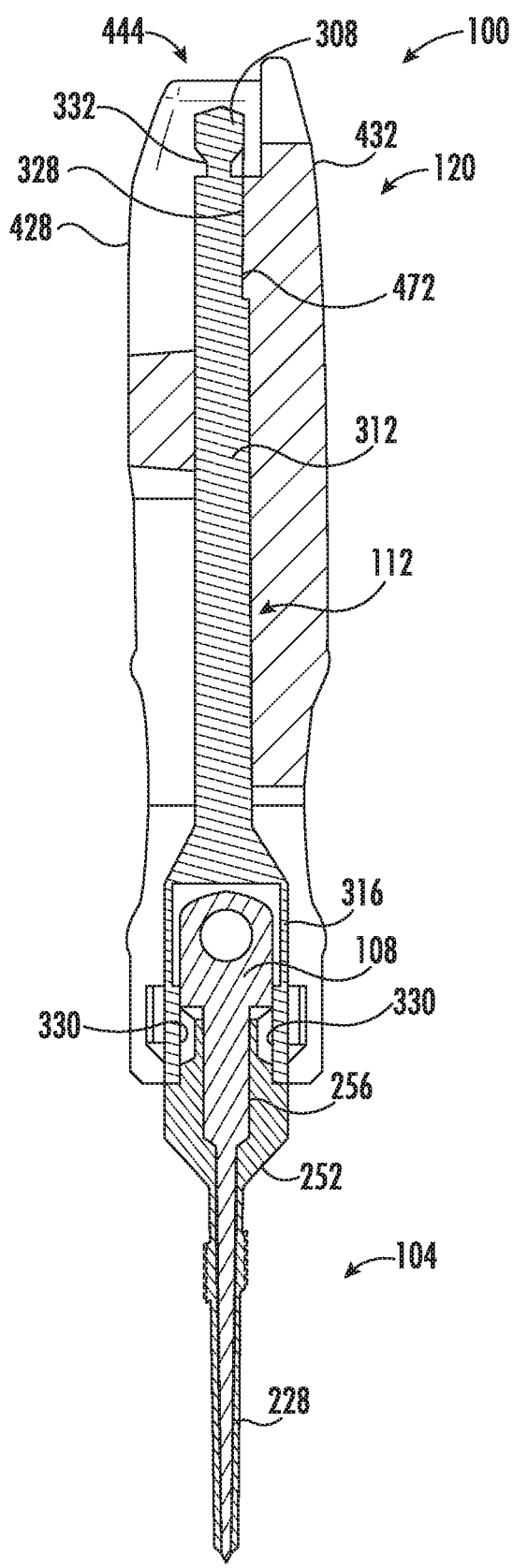
FIG. 10 is a section view of the intraosseous needle assembly taken along lines 10-10 of FIG. 8.
Figure 13:
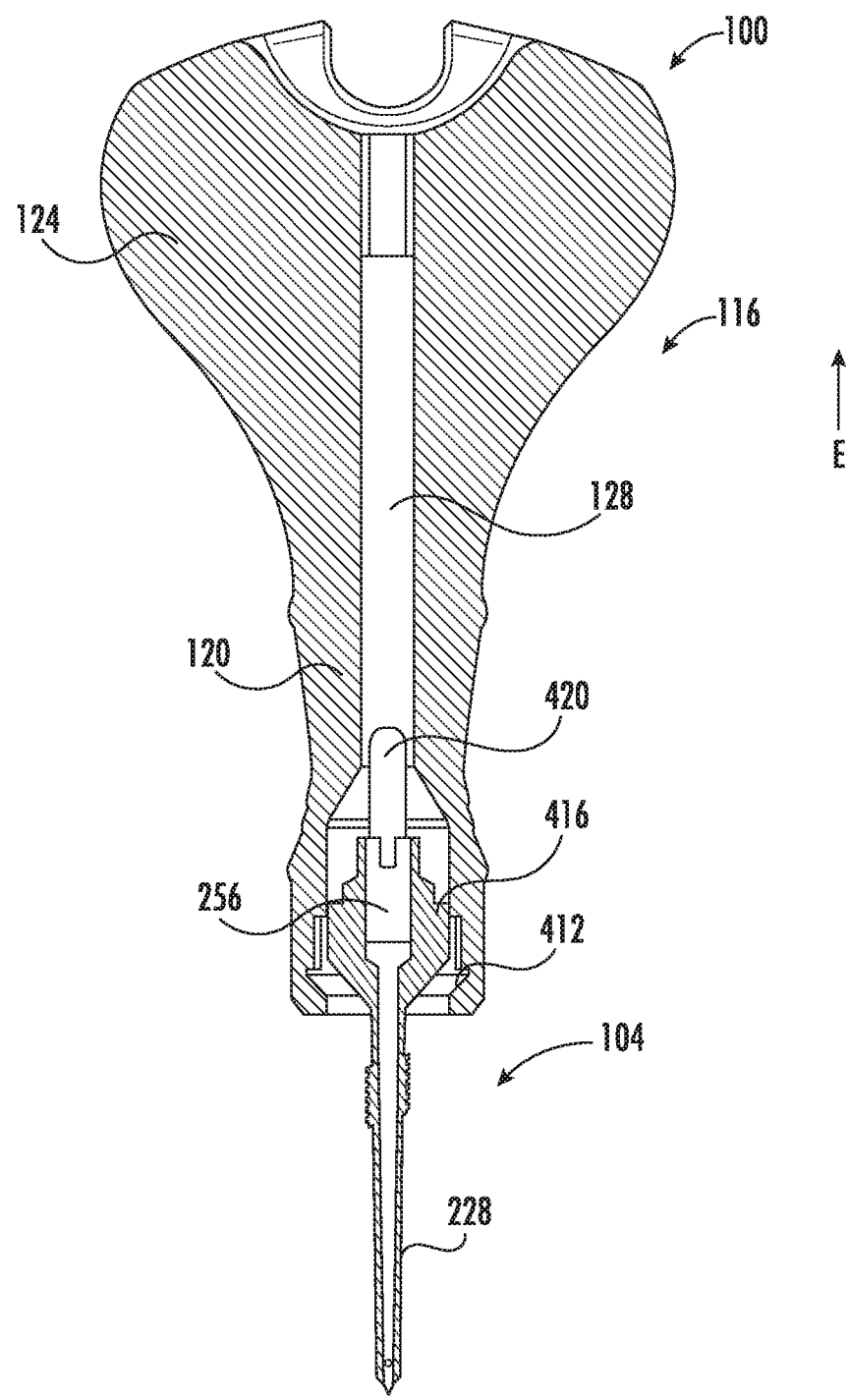
FIG. 13 is a section view of the needle engaged with the handle of the intraosseous needle assembly of FIG. 1 in another operating configuration, according to an exemplary embodiment.

FIG. 2 shows an exploded view of the needle 104 and the stylet 108. The needle 104 includes a shaft 204 and a needle head 208. The shaft 204 has a distal end 212 and a proximal end 216. The distal end 212 includes a tip 220. The proximal end 216 is coupled to the needle head 208. The shaft 204 is hollow (shown in FIGS. 9 and 13) such that a wall 224 that runs a length of the shaft 204 from the distal end 212 to the proximal end 216 defines an inner channel 228 (FIGS. 10 and 13). As illustrated in FIG. 2, in some embodiments, one or more fenestrations 232 may be positioned along the shaft 204. The one or more fenestrations 232 provide a passage through the wall 224 into the inner channel 228. In another embodiment, the shaft 204 does not include any fenestrations. In some embodiments, the shaft 204 may be substantially smooth-sided. In some embodiments, the shaft 204 includes one or more threads 236 that extend from the wall of the shaft 204 along a proximal portion of the shaft 204, such that the threads 236 are positioned at or adjacent the proximal end 216 of the shaft 204. The threads 236 may engage the needle 104 with the bone's hard cortex to prevent or reduce the risk of needle movement, such as needle back out. The threads 236 may also prevent fluid infused into the bone through the needle 104 from escaping from the interior of the bone along the boundary between the needle 104 and the bone's cortex.

Figure 6:
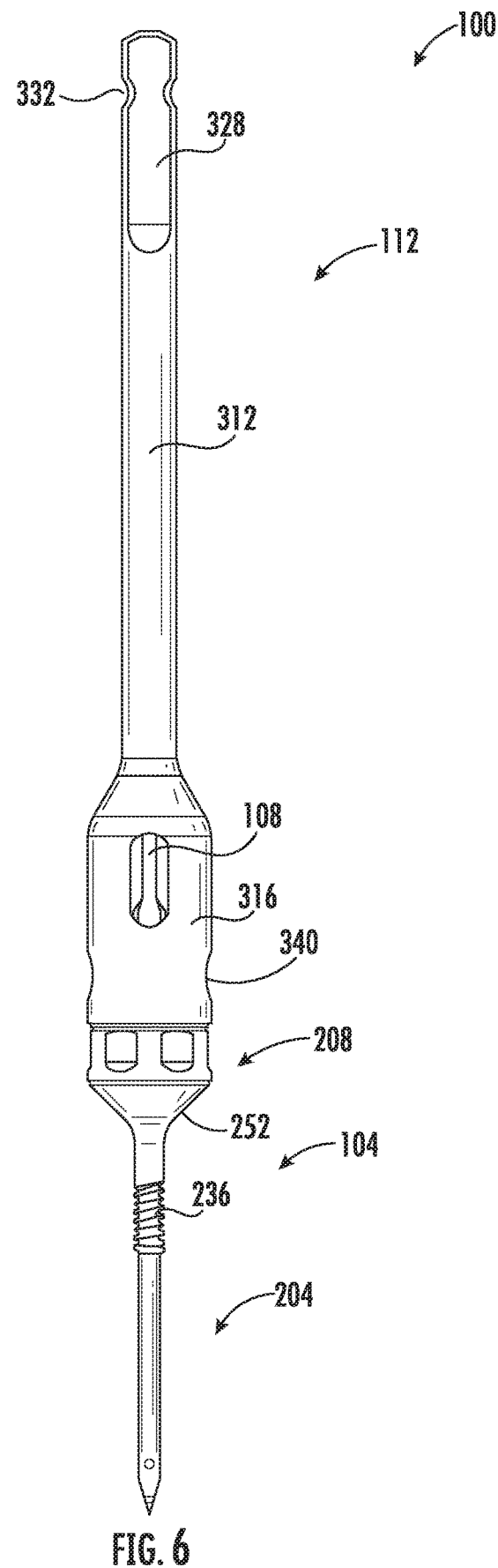
FIG. 6 is a rear view of the driving shaft engaged with the needle at the stylet in another operating configuration of the intraosseous needle assembly of FIG. 1, according to an exemplary embodiment.

The needle head 208 is coupled to the proximal end 216 of the shaft 204. The needle head 208 includes a fitting 240, a geometric torque structure 244 having at least two opposing flat surfaces 248, and a cone 252 (FIG. 6). In the illustrated embodiment, the geometric torque structure 244 is a substantially hexagonal structure positioned between the fitting 240 and the shaft 204, and the cone 252 is positioned between the geometric torque structure 244 and the shaft 204.

In some embodiments, the geometric torque structure 244 includes six opposing flat surfaces 248 equally spaced about a circumference of the geometric torque structure 244. Other embodiments may include a different number of opposing flat surfaces 248 arranged in a different configuration. Torque may be applied to the geometric torque structure 244 to engage, tighten, loosen or disengage the needle 104 in the bone. A counter-torque may be applied to the geometric torque structure 244 to counteract a torque applied to the fitting 240 and/or the latching mechanism 260 when engaging, tightening, loosening, or disengaging tubing. As used herein, the counter-torque is of substantially equal magnitude and substantially opposite direction to the torque applied to the fitting 240 and/or the latching mechanism 260 when engaging, tightening, loosening or disengaging tubing. In some embodiments, the handle 116 may be used to apply a counter-torque to the geometric torque structure 244.

The cone 252 extends between the geometric torque structure 244 and the shaft 204. A diameter of the cone 252 decreases from an end proximate the geometric torque structure 244 and an end proximate the shaft 204. The cone 252 may be configured to push aside anatomical features proximate to the target bone with minimal disruption when the needle 104 is deployed in an intraosseous infusion procedure.

A head channel 256 aligned with the inner channel 228 of the shaft 204 extends through the needle head 208 and the cone 252 (FIGS. 10 and 13). The fitting 240 includes a latching mechanism 260, a pair of substantially parallel side walls defining flat surfaces 264, and one or more slots 268. The one or more slots 268 may be configured to receive a standard flat-head screw driver, and may also receive a protrusion 292 of the stylet 108.

The latching mechanism 260 may be configured to allow the fitting 240 to engage with a standard fluid fitting such as a Luer fitting, or to fit with a specialized fluid input system. For example, the latching mechanism 260 may include threading that can be engaged with corresponding threading on a standard fluid fitting. Infusion fluid may then be supplied to the needle 104 via the fitting 240.

The pair of substantially parallel flat surfaces 264 extend from the geometric torque structure 244 and are substantially parallel to the shaft 204. The substantially parallel flat surfaces 264 may be configured to engage opposing flat surfaces 330 inside a socket 316 of the driving shaft 112. The driving shaft 112 may be engaged with a chuck of a drill. The drill may be a commercially-available surgical drill or a standard power drill, such as on a general-purpose drill marketed for use in carpentry or other non-medical applications. In some embodiments, the intraosseous needle assembly 100 can only be used with a surgical or general power drill when the needle 104 receives the stylet 108, but in other embodiments the needle 104 may engage with a drill without the stylet 108.

The stylet 108 includes a stylet head 276 and a stylet shaft 280. The stylet shaft 280 can be positioned within the head channel 256 and the inner channel 228 such that the stylet head 276 abuts the needle head 208. The stylet head 276 has a proximal surface 284 and a distal surface 288. The proximal surface 284 is configured to be grasped by an operator to insert or remove the stylet 108 from the needle 104. The stylet 108 may be freely removed from the needle 104 and inserted into the needle 104 as needed. The distal surface 288 includes one or more protrusions 292 that can be received in the one or more slots 268 of the needle 104.

Figure 3:
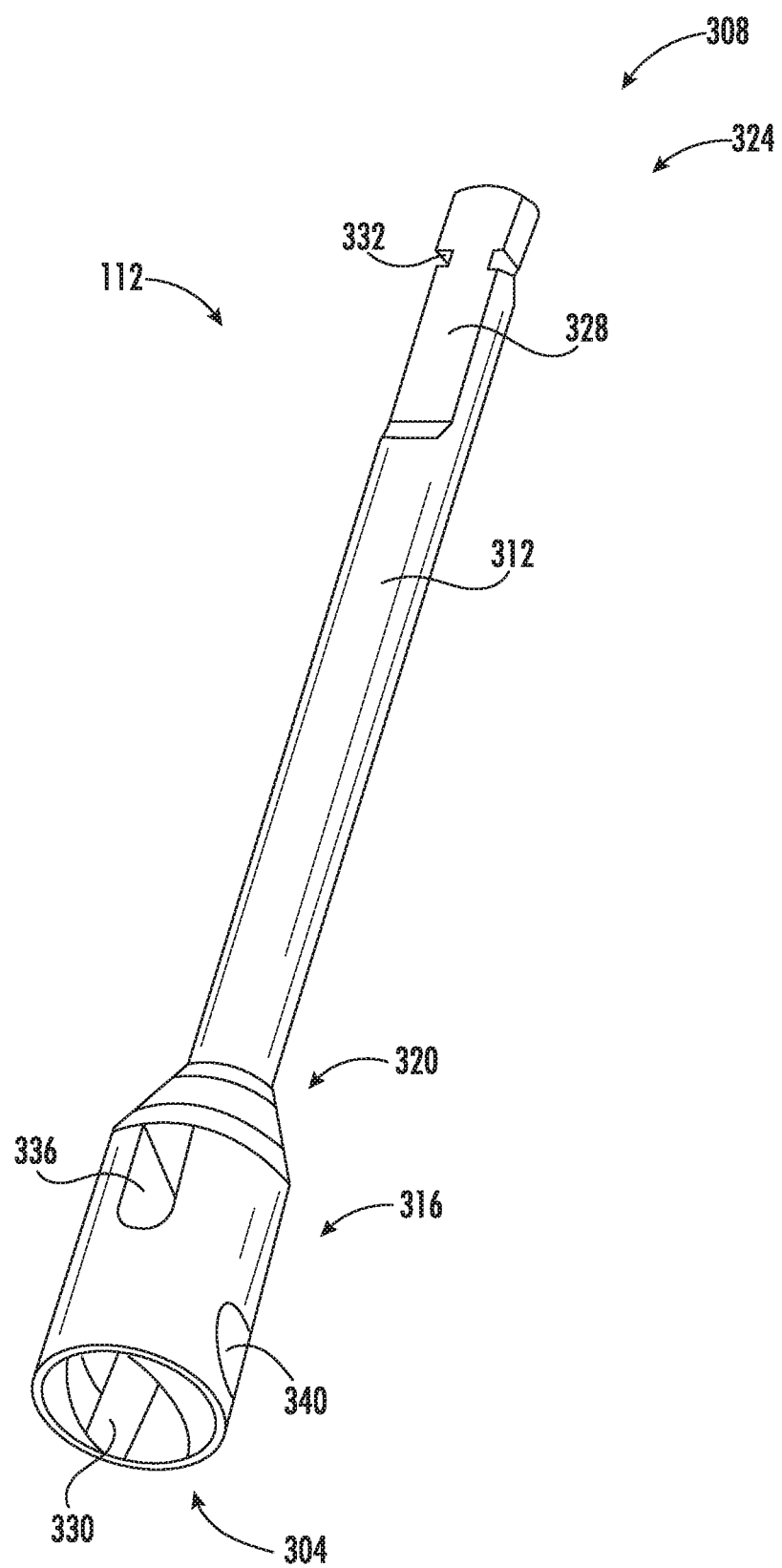
FIG. 3 is a perspective view of the driving shaft of the intraosseous needle assembly of FIG. 1, according to an exemplary embodiment.

FIG. 3 illustrates a perspective view of the driving shaft 112. The driving shaft 112 is configured to extend through the channel 128 of the handle 116. The driving shaft 112 includes a distal end 304, a proximal end 308, a shaft 312, and a socket 316. The shaft 312 includes a distal end 320 and a proximal end 324. The proximal end 324 includes a substantially flat driving surface 328 configured to engage a similar surface on the handle 116 to manually drive the needle 104 into the bone, as described in greater detail below. In some embodiments, the proximal end 324 includes a notch 332 configured to engage a drill chuck.

The socket 316 is positioned at the distal end 304 of the driving shaft 112. The socket 316 is configured to engage the proximal end 216 of the needle 104. In some embodiments, an interior of the socket 316 includes opposing flat surfaces 330 configured to engage the flat surfaces 264 of the needle 104 such that rotation of the driving shaft 112 causes rotation of the needle 104. In the illustrated embodiment, the socket 316 includes a slot 336 for visualization of the stylet 108. An exterior surface of the proximal end 308 includes one or more grooves 340 configured to engage the handle 116.

Figure 4:
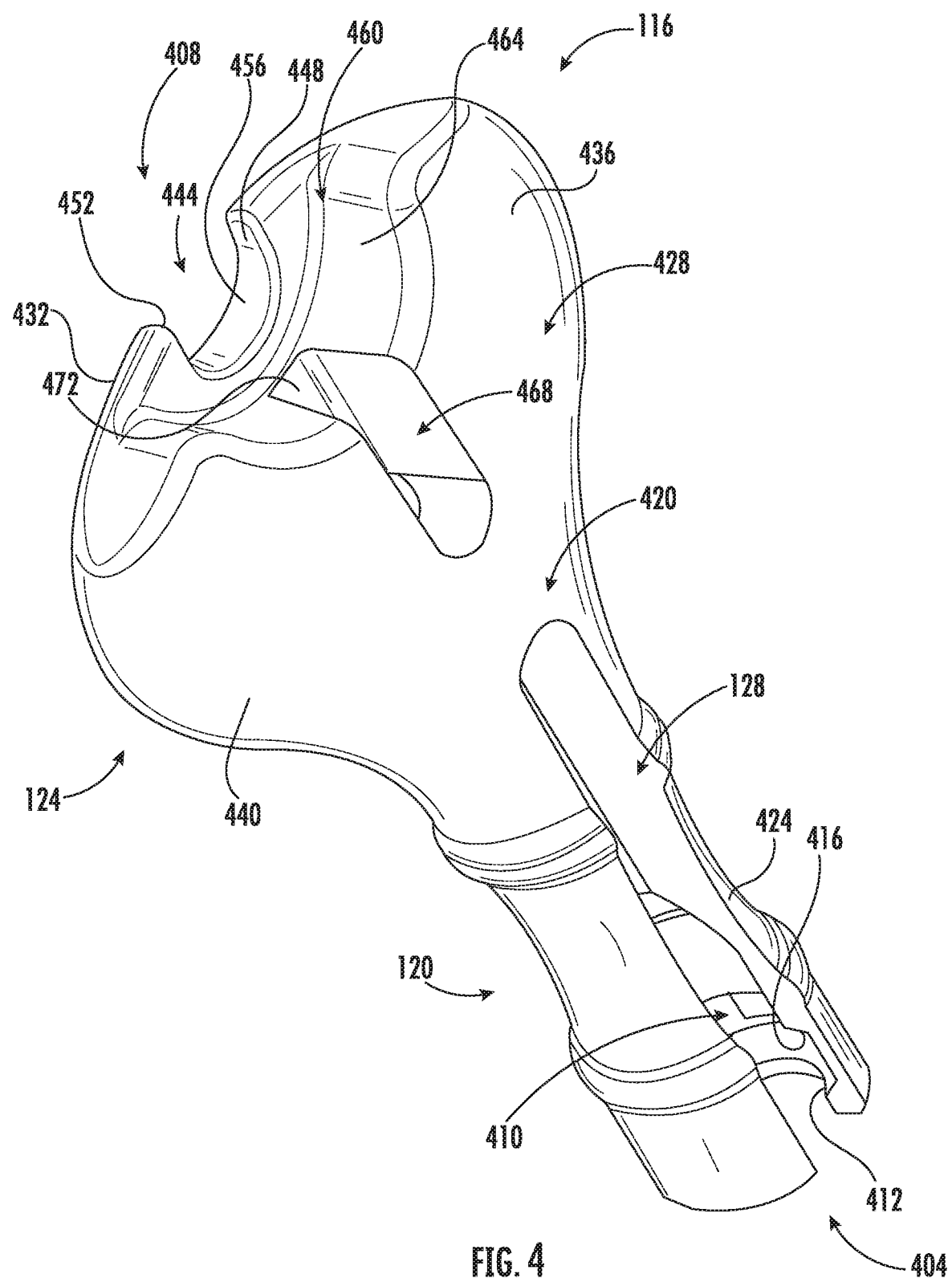
FIG. 4 is a perspective view of the handle the intraosseous needle assembly of FIG. 1, according to an exemplary embodiment.
Figure 5:
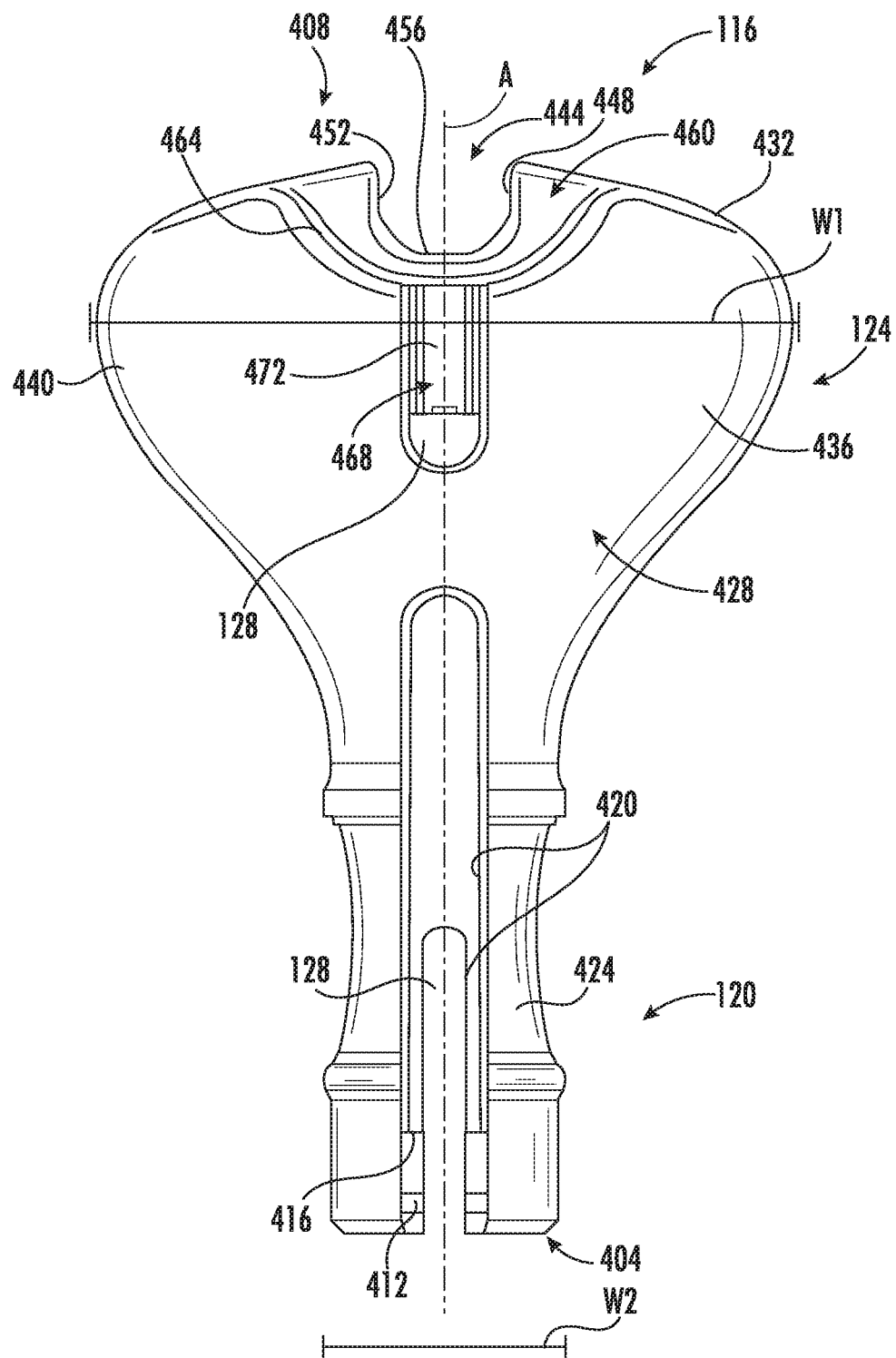
FIG. 5 is a front view of the handle of the intraosseous needle assembly of FIG. 1, according to an exemplary embodiment.

FIGS. 4 and 5 illustrate perspective and front views of the handle 116, respectively. The handle 116 has a distal end 404 and a proximal end 408. The handle 116 includes the cylindrical body portion 120, the handle portion 124, and a channel 128. The cylindrical body portion 120 defines a longitudinal axis A (FIG. 5) of the handle 116. The channel 128 extends through both the cylindrical body portion 120 and the handle portion 124 along the longitudinal axis A.

The cylindrical body portion 120 is configured to engage the driving shaft 112. The channel 128 includes an enlarged portion 410 at or proximate the distal end 404 of the cylindrical body portion 120 to receive the proximal end 216 of needle head 208. As is best shown in FIG. 4, the enlarged portion 410 of the channel 128 includes a first rib or flange 412 and a second rib or flange 416 configured to engage the distal end 316 of the driving shaft 112. The cylindrical body portion 120 includes a pair of first and second opposing longitudinal slots 420 that provide an opening between an outer surface 424 of the cylindrical body portion 120 and the channel 128. The pair of opposing longitudinal slots 420 may allow deflection of the cylindrical body portion 120. The pair of opposing longitudinal slots 420 are configured to expand when engaging the proximal end 216 of the needle 104 to allow the distal end of the cylindrical body portion 120 to receive the proximal end 216 of the needle 104 when the handle 116 is used as a forceps. The pair of opposing longitudinal slots 420 is configured to allow the walls of the cylindrical body portion 120 to contract substantially inward (e.g., towards the channel 128) so that an operator can squeeze the cylindrical body portion 120 to secure the proximal end 216 of the needle 104 within the enlarged portion 410 of the channel 128.

The handle portion 124 has a substantially flattened bulb shape and opposing first 428 and second 432 (FIG. 9) planar surfaces. The handle portion 124 is flared such that a width $W_1$ (FIG. 5) of the handle portion 124 proximate the proximal end 408 of the handle 116 is wider than a width $W_2$ (FIG. 5) of the cylindrical body portion 120. The handle portion 124 has a first lobe 436, a second lobe 440, and a notch 444 positioned between the first lobe 436 and the second lobe 440. In the illustrated embodiment, the notch 444 is positioned along the longitudinal axis A. The notch 444 includes first and second opposing flat surfaces 448, 452 connected by a curved surface 456. The first and second opposing flat surfaces 448, 452 are configured to engage the flat surfaces 248 of the geometric torque structure 244 of the needle head 208 in the operating configuration shown in FIGS. 11-12. In the embodiment illustrated in FIGS. 4-5, the handle portion 124 includes a cavity 460 that extends through the first planar surface 428 but not the second planar surface 432. The cavity 460 is substantially perpendicular to the notch 444. The cavity 460 is defined by a curved sidewall 464 and is substantially aligned with the longitudinal axis A. As described in greater detail below, the cavity 460 is configured to provide clearance for tubing coupled to the needle head 208 while the handle 116 is engaged with the needle 104 in the operating configuration shown in FIGS. 11-12.

Figure 8:
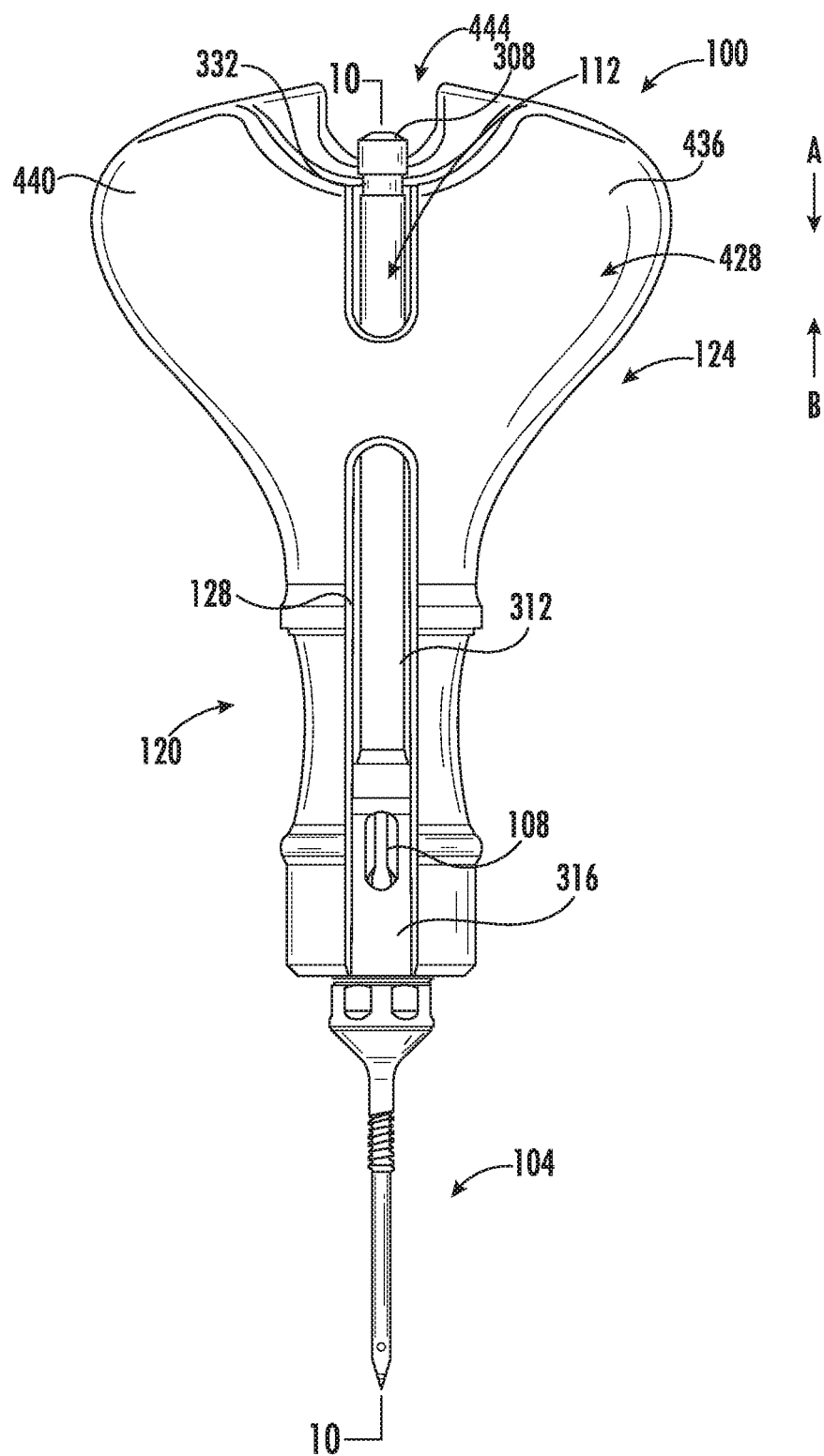
FIG. 8 is a front view of the intraosseous needle assembly in the operating configuration of FIG. 1, according to an exemplary embodiment.

The handle portion 124 includes a slot 468 that forms an opening between the channel 128, the cavity 460, and the first planar surface 428 of the handle portion 124. The slot 468 includes a flat driving surface 472 configured to engage the driving surface 328 of the driving shaft 112. As shown in FIGS. 1 and 8-9, the driving shaft 112 extends through the channel 128 and protrudes into the notch 444 in operating configurations in which the driving shaft 112 is engaged with the handle 116.

FIG. 6 illustrates the needle 104, the stylet 108, and the driving shaft 112 in a first operating configuration of the intraosseous needle assembly 100. In the first operating configuration, the stylet 108 is received within the inner channel 228 of the needle 104. The needle head 208 is engaged within the socket 316 of the driving shaft 112. The flat surfaces 264 of the needle head 208 are engaged with the opposing flat surfaces 330 within the socket 316 of the driving shaft 112 such that rotation of the driving shaft 112 rotates (e.g., drives) the needle 104. In some embodiments, a drill chuck may be engaged with the notch 332 of the driving shaft 112 to drive the needle 104 into bone.

Figure 7:
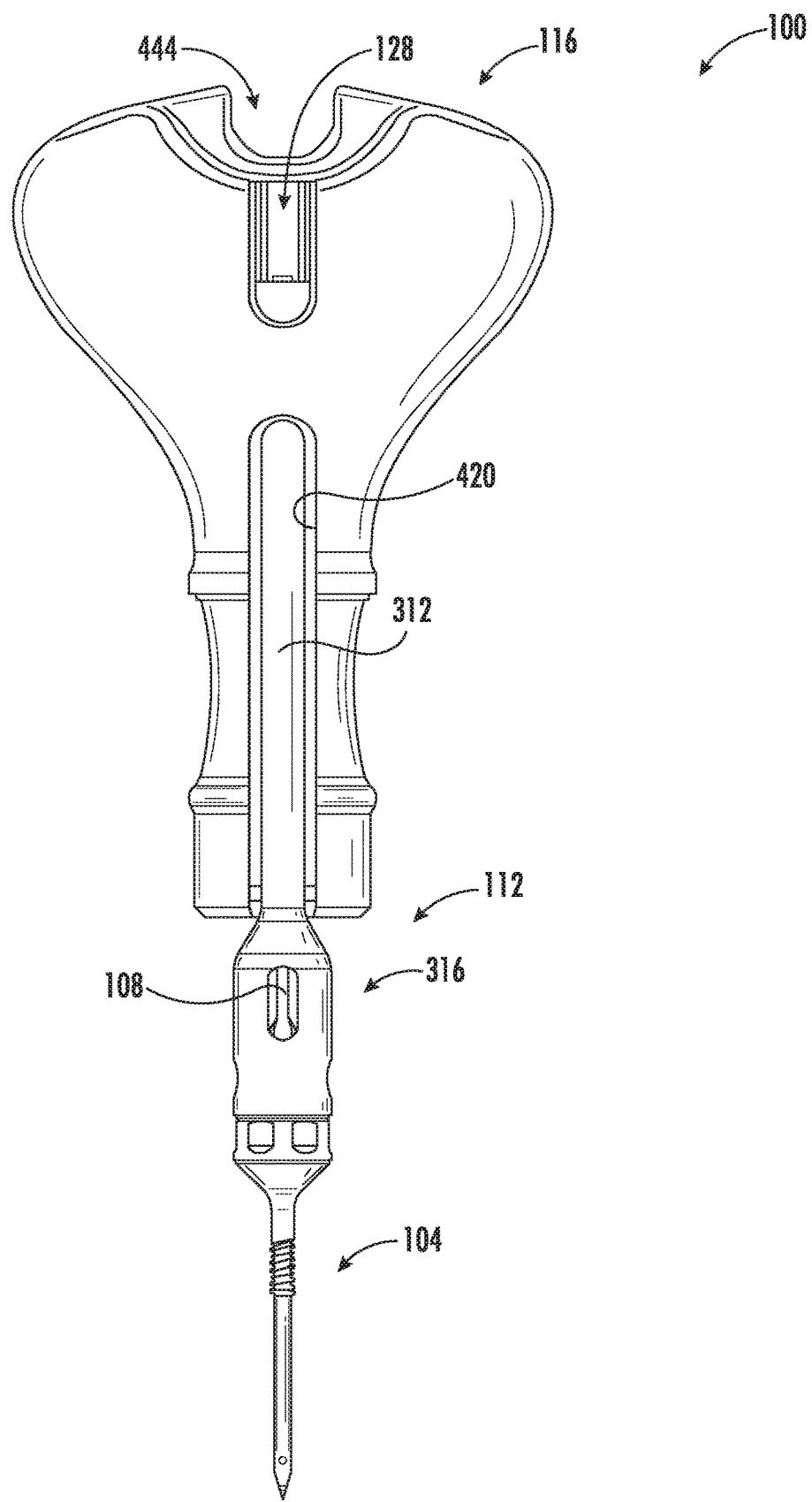
FIG. 7 is a front view of the driving unit engaged with the needle and the stylet and displaced relative to the handle of the intraosseous needle assembly of FIG. 1, according to an exemplary embodiment.

As illustrated in FIG. 7, the handle 116 can be engaged with the driving shaft 112, the needle 104, and the stylet 108 to form a second operating configuration of the intraosseous needle assembly 100.

More specifically, and as is best illustrated in FIG. 10, an operator can slide the driving shaft 112 through channel 128 in the handle 116 until the distal end 304 of the driving shaft 112 and the proximal end of the needle 104 are positioned within the enlarged portion 410 of the channel 128 of the handle 116, the flat driving surface 328 of the driving shaft 112 is in contact with the flat driving surface 428 of the channel 128, and the proximal end 308 of the driving shaft 112 extends through the notch 444 of the handle 116.

FIGS. 8-10 illustrate the needle 104, the stylet 108, the driving shaft 112, and the handle 116 in the second operating configuration of the intraosseous needle assembly 100. In the second operating configuration, the handle 116 is engaged with the needle 104, the stylet 108 and the driving shaft 112 such that an operator can manually insert the needle 104 into the matrix of a bone by manually pushing the handle towards the matrix of the bone and rotating the handle 116. FIGS. 8 and 9 illustrate front and rear views of the intraosseous needle assembly 100 in the second operating configuration. FIG. 10 illustrates a section view of FIG. 8 taken along lines 10-10. In the second operating configuration, the driving shaft 112 and the proximal ends of the needle 104 and the stylet 108 are positioned within the channel 128. As is best illustrated in FIG. 10, the driving surface 328 of the driving shaft 112 is engaged with the driving surface 472 within the channel 128 such that rotation of the handle 116 rotates (e.g., drives) the driving shaft 112 with the handle 116. The handle 116 transfers the rotation and pushing forces to the needle 104 to allow the needle 104 to penetrate the bone. The opposing flat surfaces 330 of the driving shaft 112 are engaged with the flat surfaces 264 of the needle head 208, such that the needle 104 rotates with (e.g., is driven by) the driving shaft 112 as the handle 116 is rotated.

In the illustrated embodiment, the stylet 108 is positioned within the inner channel 228 of the needle 104 in the first and second operating configurations to prevent bone fragments and/or other debris from entering the inner channel 228 as the needle 104 is engaged with the bone. The proximal end 308 of the driving shaft 112 extends into the cavity 460 and the notch 444. Accordingly, after the operator has secured the needle 104 within the matrix of the bone, the operator can press down (e.g., as indicated by arrow A) on the proximal end 308 of the driving shaft 112 while pulling up (e.g., as indicated by arrow B) on the handle 116 to disengage the handle 116 from the driving shaft 112 to enable the operator to engage the driving shaft 112 with a chuck of a drill or to enable the operator to use the handle 116 as a countertorque or a forceps. In other embodiments, the operator may remove the handle 116, the driving shaft 112, and the stylet 108 from the needle 104 as a single unit.

Figure 11:
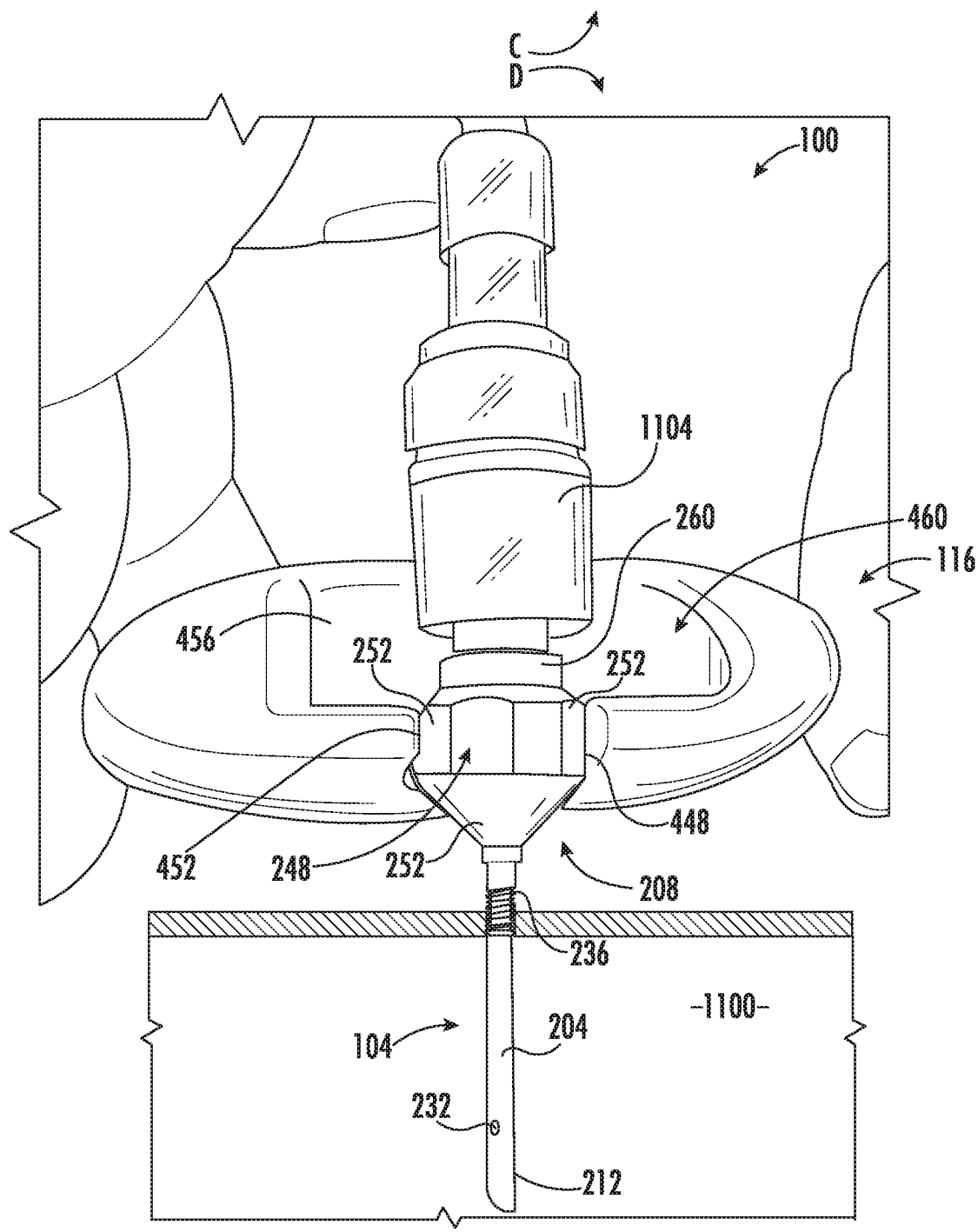
FIG. 11 is a side view of the needle and the handle of intraosseous needle assembly of FIG. 1 in another operating configuration, according to an exemplary embodiment.
Figure 12:
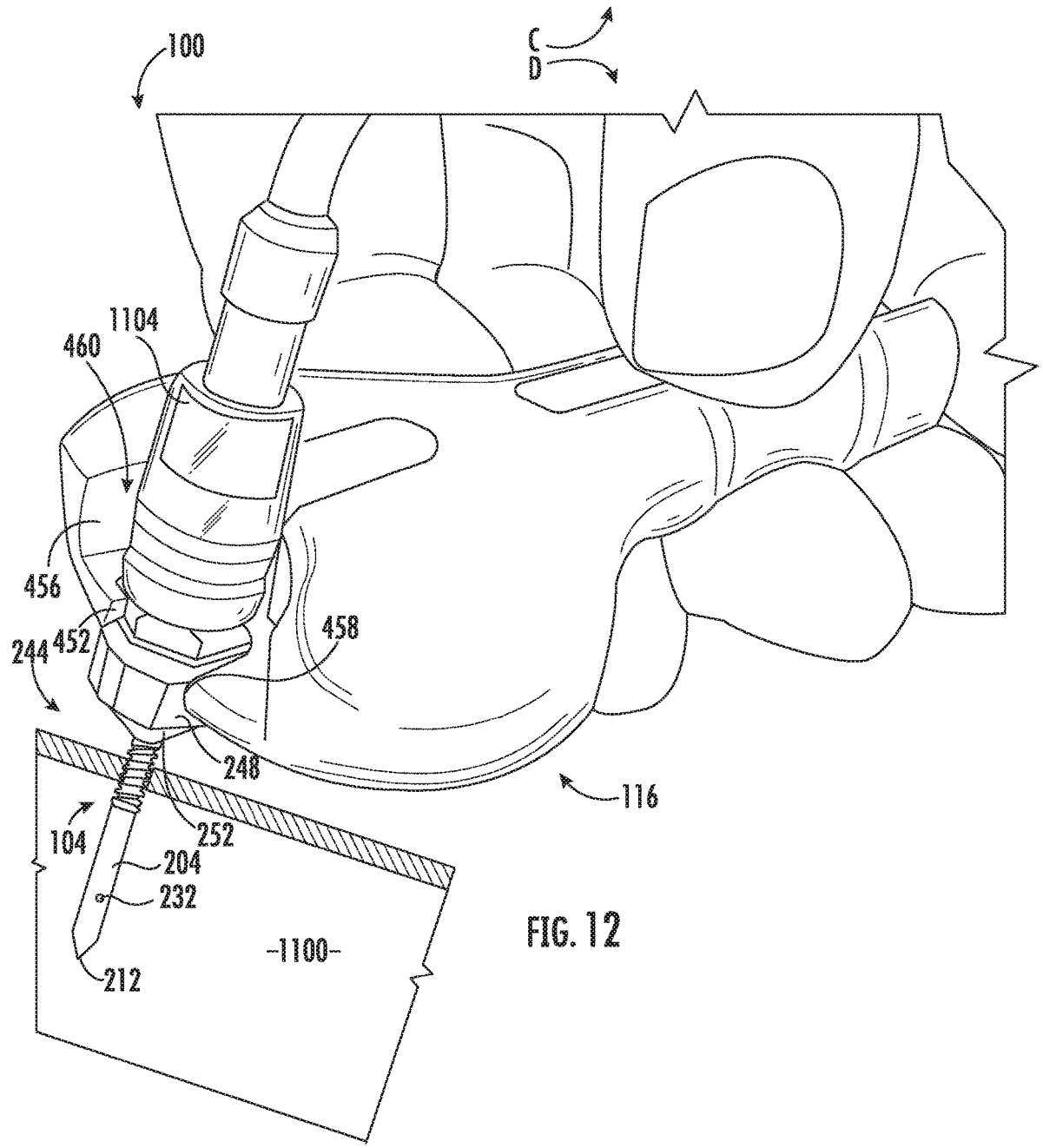
FIG. 12 is a perspective view of the needle and the handle of intraosseous needle assembly of FIG. 1 in the operating configuration of FIG. 11, according to an exemplary embodiment.

FIGS. 11 and 12 illustrate the needle 104 and the handle 116 in a third operating configuration of the intraosseous needle assembly 100. As illustrated in FIGS. 11 and 12, the needle 104 is deployed within a bone 1100. The distal end 212 of the needle 104 is positioned within the bone 1100 and the needle head 208 extends above the bone 1100. In the illustrated embodiment, at least a portion of the threads 236 are engaged with the bone 1100 to prevent the needle 104 from backing out of the bone 1100. As illustrated in FIGS. 11 and 12, the needle head 208 is engaged with tubing 1104 (e.g., threadably engaged or friction-fit to the needle head 208). During deployment of the needle 104 within the bone 1100, it may become desirable to engage or tighten the tubing 1104 to the needle head 208 (e.g., to perform an intraosseous infusion) or to loosen or remove the tubing 1104 from the needle head 208 while minimizing movement of the needle 104 within the bone 1100. Accordingly, before connection or removal of the tubing 1104, the notch 444 of the handle 116 may be engaged with the needle head 208 such that the opposing flat surfaces 248 of the geometric torque structure 244 of the needle head 208 are engaged with the first and second opposing surfaces 448, 452 of the notch 444. The latching mechanism 260 of the needle head 208 and the tubing 1104 are positioned within the cavity 460 of the handle 116 when the notch 444 is engaged with the latching mechanism 260 of the needle head 208. When installing or removing tubing, the operator of the intraosseous needle assembly 100 can hold the tubing 1104 with one hand and apply a torque to the tubing 1104 to engage, tighten, loosen, or disengage the tubing 1104 with the latching mechanism 260 of the needle head 208 (e.g., as indicated by arrow C). Simultaneously, the operator can grasp the handle 116 with the other hand and apply a counter-torque to the handle 116 (e.g., as indicated by arrow D) to prevent the needle 104 from twisting relative to the bone as the tubing 1104 is being connected to or removed from the latching mechanism 260 of the needle head 208.

FIG. 13 illustrates the needle 104 and the handle 116 of the intraosseous needle assembly 100 in a fourth operating configuration, which may be used to remove the needle 104 from the bone (not shown). In the fourth operating configuration, the needle head 208 is positioned within the enlarged portion 410 of the channel 128 between the flanges 412, 416. The operator can squeeze the sides of the cylindrical body portion 120 of the handle 116 to apply a force on the sides of the needle head 208. The opposing longitudinal slots 420 allow the cylindrical body portion 120 to contract, allowing the operator to grasp the needle head 208 with the handle. The operator can then use the handle 116 to extract the needle 104 from the bone. For example, in embodiments in which when the threads 236 of the needle 104 are engaged with the bone, the operator can then use the handle 116 to twist the needle 104 relative to the bone to disengage the needle 104 from the bone. The operator can use the handle 116 to exert an upward force (e.g., as indicated by arrow E) on the needle head 208 to extract the needle 104 from the bone.

When deploying the intraosseous needle assembly 100, in embodiments that include the stylet 108, the operator of the intraosseous needle assembly 100 engages the stylet 108 with the needle 104 to position the stylet shaft 280 with the inner channel 228 of the needle 104. Positioning the stylet shaft 280 within the inner channel 228 of the needle 104 may prevent bone particles and/or other bodily materials from blocking the inner channel 228 during insertion.

The operator then engages the driving shaft 112 with the needle 104 in the first operating configuration, which is illustrated in FIG. 6. Engaging the driving shaft 112 with the needle 104 includes positioning the needle head 208 within the socket 316 of the driving shaft 112 such that the opposing flat surfaces 330 within the socket 316 are engaged with the flat surfaces 264 of the needle head 208. Engaging the opposing flat surfaces 330 of the socket 316 with the flat surfaces 264 of the needle head 208 allows rotation of the driving shaft 112 to rotate (e.g., drive) the needle 104.

In some embodiments, the operator may engage the driving shaft 112 with the handle 116, as illustrated in FIG. 7. Engaging the driving shaft 112 with the handle 116 includes sliding the driving shaft 112 through the channel 128 in the handle 116 so that the socket 316 of the driving shaft 112 is engaged within the enlarged portion 410 of the channel 128. FIGS. 1, 8-10 illustrate the driving shaft 112 engaged with the handle 116 in the second operating configuration. The operator may manually push the handle 116 towards the bone and rotate the handle 116 to drive the needle 104 into the bone. As the handle 116 is rotating, the engagement between the flat driving surface 328 of the driving shaft 112 and the flat driving surface 472 within the channel 128 of the handle 116 rotates (e.g, drives) the driving shaft 112. The opposing flat surfaces 330 of the driving shaft 112 rotate the flat surfaces 264 of the needle 104 to engage the needle 104 with the patient's bone. The operator may grasp the lobes 436, 440 when using the handle 116 to engage the needle 104 with the patient's bone.

In another embodiment, the operator may engage the notch 332 of the proximal end 324 of the driving shaft 112 with a chuck of a drill. The operator may then actuate the drill to rotate the driving shaft 112 to engage the needle 104 with a patient's bone. After engaging the needle 104 with the bone, the operator may remove the driving shaft 112 and the stylet 108. The operator may then use the needle 104 to administer treatments to the patient.

As illustrated in FIGS. 1, 8-10, in the second operating configuration, the proximal end 308 of the driving shaft 112 extends through the notch 444 of the handle 116, which facilitates disengagement of the driving shaft 112 from the handle 116. In embodiments in which the handle 116 is used to engage the needle 104 with the bone, the operator may push down on the portion of the proximal end 308 of the driving shaft 112 while grasping the handle 116 to release the driving shaft 112 from the handle 116. The operator may then lift the handle 116 away from the driving shaft 112. After engaging the needle 104 with the bone, the operator may remove the driving shaft 112 and the stylet 108.

After the needle 104 has been deployed in the patient's bone, the operator may use the needle 104 in an infusion procedure. During the infusion procedure, fluid may be introduced into the needle head 208. For example, tubing may be engaged with the latching mechanism 260 of the fitting 240, and then fluid may be introduced into the needle head 208 through the tubing. Such fluid may enter the needle 104 through the head channel 256 (FIG. 10) and flow to inner channel 228 of the shaft 204. The fluid may exit the shaft 204 through the fenestrations 232 or the tip 220.

FIGS. 11-12 illustrate engagement of the handle 116 and the needle 104 when engaging, tightening, loosening, or disengaging the tubing 1104 from the needle head 208. In embodiments in which the tubing 1104 is engaged with the latching mechanism 260 of the needle 104, the operator may need to apply torque to disengage the tubing 1104 from the latching mechanism 260. Applying torque to the needle 104 and/or the tubing 1104 may move or otherwise disturb the needle 104 and/or cause the needle 104 to move relative to the bone 1100. Accordingly, before engaging, tightening, loosening, or disengaging the tubing 1104 from the latching mechanism 260, the operator engages two of the opposing flat surfaces 248 of the geometric torque structure 244 with the opposing flat surfaces 448, 452 of the notch 444 of the handle 116. The operator then grasps the tubing 1104 with one hand and applies a first torque in a first direction indicated by arrow C in FIGS. 11-12 to engage, tighten, loosen or disengage the tubing 1104 from the needle 104 and applies a counter-torque in a second direction indicated by arrow D FIGS. 11-12 to counter the torque, thereby reducing a likelihood that the needle 104 will be moved relative to the bone 1100 when engaging, tightening, loosening, or disengaging the tubing 1104 from the latching mechanism 260 of the needle 104.

In some embodiments, the operator may use the handle 116 to remove the needle 104 from the bone. For example, the operator may engage the needle head 208 with the channel 128 of the handle 116 so that the needle head 208 is positioned within the enlarged portion 410 of the channel 128 and positioned between the flanges 412, 416 as shown in the operating configuration illustrated in FIG. 13. The opposing longitudinal slots 420 may splay apart so that the enlarged portion 410 of the channel 128 can fit over the needle head 208. The operator can squeeze the cylindrical body portion 120 of the handle 116 to grasp the needle head 208. The opposing longitudinal slots 420 may allow the sides of the cylindrical body portion 120 to move inward (e.g., towards the axis A) to facilitate grasping the needle head 208. In embodiments in which the needle 104 includes the threads 236 and the threads 236 are engaged with the bone, the operator may grasp the needle head 208 with the handle 116, squeeze the sides of the cylindrical body portion 120 to substantially immobilize the needle 104 relative the handle 116, and then rotate the handle 116 to disengage the threads 236 from the bone. In embodiments in which the needle 104 does not include the threads 236 or when the threads 236 are not engaged with the bone, the operator may grasp the needle head 208 with the handle 116, squeeze the sides of the cylindrical body portion 120 to substantially immobilize the needle 104 relative the handle 116, and then pull the handle 116 away from the bone to disengage the shaft 204 of the needle 104 from the bone.

The construction and arrangement of the devices and methods as shown in the various exemplary embodiments are illustrative only. Although only a few embodiments have been described in detail in this disclosure, many modifications are possible (e.g., variations in sizes, dimensions, structures, shapes and proportions of the various elements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A system comprising:
    an intraosseous needle including a distal end configured for insertion into a bone and a proximal end configured to extend from the bone; and
    a handle configured to releasably engage the intraosseous needle, the handle including:
        a cylindrical body portion including a distal end configured to receive a proximal end of a driving shaft engaged with the intraosseous needle, wherein the cylindrical body portion is configured to receive the proximal end of the driving shaft engaged with the intraosseous needle in a first operating configuration for inserting the intraosseous needle into the bone;
        a handle portion extending from the cylindrical body portion having a bulb-like cross-sectional shape and opposing first and second substantially planar surfaces, wherein the handle portion comprises a notch configured to engage the proximal end of the intraosseous needle in a second operating configuration for immobilizing the intraosseous needle relative to the bone; and
        a channel configured to receive the proximal end of the driving shaft.

2. The system of claim 1, wherein the notch of the handle portion includes a curved surface connecting a first pair of opposing flat surfaces, the opposing flat surfaces configured to engage a second pair of opposing flat surfaces of the proximal end of the intraosseous needle.

3. The system of claim 1, further comprising the driving shaft including a distal end configured to engage the proximal end of the intraosseous needle and a proximal end including a flat portion configured to be driven.

4. The system of claim 3, wherein the flat portion of the driving shaft is configured to engage a chuck of a drill.

5. The system of claim 3, wherein the channel includes a flat portion configured to engage and drive the flat portion of the driving shaft.

6. The system of claim 3, wherein the proximal end of the driving shaft protrudes from the channel such that the proximal end of the driving shaft can be pressed to disengage the driving shaft from the handle.

7. The system of claim 1, wherein the intraosseous needle further comprises a shaft extending to the distal end and a head portion extending to the proximal end, and wherein the shaft comprises a plurality of threads.

8. The system of claim 1, wherein the cylindrical body portion includes first and second opposing slots that provide an opening between an outer surface of the cylindrical body portion and the channel.

9. A handle configured to engage an intraosseous needle including a distal end configured for insertion into a bone and a proximal end configured to extend from the bone, the handle comprising:
    a cylindrical body portion including a distal end configured to receive a proximal end of a driving shaft engaged with the intraosseous needle, the cylindrical body portion defining a longitudinal axis of the handle;
    a flared handle portion having a width larger than a width of the cylindrical body portion, the flared handle portion including a first lobe, a second lobe, and a notch positioned between the first lobe and the second lobe, wherein the notch includes a curved surface connecting a first pair of opposing flat surfaces, the opposing flat surfaces configured to engage a second pair of opposing flat surfaces of the proximal end of the intraosseous needle while threadably engaging a component with threads of the proximal end of the intraosseous needle; and
    a channel extending between a proximal end of the flared handle portion and the distal end of the cylindrical body portion along the longitudinal axis.

10. The handle of claim 9, wherein the distal end of the cylindrical body portion receives the proximal end of the driving shaft engaged with the intraosseous needle in a first operating configuration configured for inserting the intraosseous needle into the bone.

11. The handle of claim 9, wherein the distal end of the cylindrical body portion includes first and second opposing slots that provide an opening between an outer surface of the cylindrical body portion and the channel.

12. The handle of claim 9, wherein a portion of the channel proximate the distal end of the cylindrical body portion comprises a first rib configured to engage a head portion of the intraosseous needle.

13. The handle of claim 9, wherein the channel is configured to receive the driving shaft coupled to the proximal end of the intraosseous needle.

14. The handle of claim 13, wherein a portion of the channel proximate a proximal end of the channel includes a flat surface configured to engage a flat surface of the proximal end of the driving shaft to drive the driving shaft.

15. The handle of claim 14, wherein the proximal end of the driving shaft protrudes into the notch such that the proximal end of the driving shaft can be pressed to disengage the driving shaft from the handle.

16. A method for inserting a medical device into an interior of a bone, the method comprising:
coupling a driving shaft to an intraosseous needle;
engaging the driving shaft and a proximal end of the intraosseous needle with a channel of a handle, the handle including:
a cylindrical body portion including a distal end configured to receive the proximal end of the intraosseous needle, and
a flared handle portion having a width larger than a width of the cylindrical body portion, the flared handle portion including a first lobe, a second lobe, and a notch positioned between the first lobe and the second lobe;
actuating the handle to insert the intraosseous needle into the bone; and
pushing on a portion of a distal end of the driving shaft that protrudes into the notch to disengage the driving shaft from the handle.

17. The method of claim 16, further comprising:
removing the driving shaft from the intraosseous needle;
engaging a first pair of opposing flat surfaces of the notch of the handle with a second pair of opposing flat surfaces of the proximal end of the intraosseous needle;
applying a first torque to a component to threadably couple the component to the proximal end of the intraosseous needle; and
applying a second torque to the intraosseous needle with the handle, the second torque substantially opposing the first torque to immobilize the intraosseous needle relative to the bone.

18. The method of claim 17, wherein the handle abuts a surface of a patient while the notch is engaged with the proximal end of the intraosseous needle.

19. The method of claim 16, further comprising:
engaging the distal end of the cylindrical body portion with the proximal end of the intraosseous needle such that the proximal end of the intraosseous needle is received with the channel;
squeezing the cylindrical body portion; and
extracting the intraosseous needle from the bone by exerting an upward force on the proximal end of the intraosseous needle with the handle.

20. The method of claim 19, wherein the cylindrical body portion comprises first and second opposing slots that extend between an outer surface of the cylindrical body portion and the channel proximate the distal end of the cylindrical body portion, the first and second opposing slots configured to expand when engaging the proximal end of the intraosseous needle to allow the distal end of the cylindrical body portion to receive the proximal end of the intraosseous needle in the channel and contract when squeezing the distal end of the cylindrical body portion to secure the proximal end of the intraosseous needle within the channel when extracting the intraosseous needle from the bone.

21. The method of claim 20, wherein a portion of the channel proximate a proximal end of the cylindrical body portion comprises a first rib configured to engage a head of the intraosseous needle.

* * * * *